(12) United States Patent
Klopfenstein et al.

(10) Patent No.: US 7,372,778 B2
(45) Date of Patent: May 13, 2008

(54) PULSOMETER WORN ON WRIST AND ASSOCIATED CONTROL METHOD

(75) Inventors: François Klopfenstein, Delémont (CH); Rolf Vetter, Cottens (CH); Philippe Renevey, Lausanne (CH); Victor Neuman, Cormondrèche (CH); Christophe Verjus, Neuchâtel (CH)

(73) Assignee: ETA SA Manufacture Horlogère Suisse, Grenchen (CH)

( * ) Notice: Subject to any disclaimer, the term of this patent is extended or adjusted under 35 U.S.C. 154(b) by 0 days.

(21) Appl. No.: 11/781,348

(22) Filed: Jul. 23, 2007

(65) Prior Publication Data

US 2008/0019218 A1   Jan. 24, 2008

(30) Foreign Application Priority Data

Jul. 21, 2006   (EP) .................................. 06117653

(51) Int. Cl.
*G04B 47/00* (2006.01)
*A61B 5/02* (2006.01)

(52) U.S. Cl. ....................................... 368/10; 600/503
(58) Field of Classification Search .................. 368/10, 368/11, 278, 281; 600/500–504
See application file for complete search history.

(56) References Cited

U.S. PATENT DOCUMENTS

| | | | |
|---|---|---|---|
| 4,063,551 A | 12/1977 | Sweeney | |
| 4,706,072 A | 11/1987 | Ikeyama | |
| 5,810,736 A * | 9/1998 | Pail | 600/500 |
| 6,241,684 B1 * | 6/2001 | Amano et al. | 600/531 |
| 6,443,906 B1 * | 9/2002 | Ting et al. | 600/490 |
| 6,811,535 B2 * | 11/2004 | Palti et al. | 600/499 |
| 7,314,450 B2 * | 1/2008 | Iwamiya et al. | 600/503 |
| 2001/0056240 A1 * | 12/2001 | Palti et al. | 600/481 |
| 2003/0065269 A1 | 4/2003 | Vetter et al. | |
| 2004/0236227 A1 | 11/2004 | Guiessaz | |
| 2006/0229520 A1 * | 10/2006 | Yamashita et al. | 600/503 |

FOREIGN PATENT DOCUMENTS

FR   2 669 819   6/1992
WO   01/95796 A1   12/2001

OTHER PUBLICATIONS

European Search Report issued in corresponding application No. EP 06 11 7653, completed Jan. 30, 2007.

* cited by examiner

*Primary Examiner*—Vit W Miska
(74) *Attorney, Agent, or Firm*—Griffin & Szipl, PC

(57) ABSTRACT

The invention proposes a pulsometer (10) comprising a case (14) which contains an electronic optical pulse measuring device (18) and an electronic circuit, a tightening wristband (16) which holds the back cover of the case (14) pressed against the wrist (12), characterized in that the electronic optical measuring device (18) includes at least two light sources (E1, E2, E3) and at least two receivers (R1, R2, R3), in that the light sources (E1, E2, E3) and the receivers (R1, R2, R3) are arranged in the form of a matrix comprising two lines (L1, L2) each oriented along an orthogonal direction to the direction (D1) of the wrist (12), and at least two columns (C1, C2, C3), oriented parallel to the direction (D1) of the wrist (12), in that each line (L1, L2) of the matrix alternately contains a light source (E1, E2, E3) and a receiver (R1, R2, R3), and each column (C1, C2, C3) of the matrix contains a light source (E1, E2, E3) and a receiver (R1, R2, R3).

The invention also proposes a control method for this pulsometer (10).

15 Claims, 3 Drawing Sheets

PULSOMETER WORN ON WRIST AND ASSOCIATED CONTROL METHOD

The present invention concerns a pulsometer that can be worn on the wrist and a control method for the same.

The invention concerns more specifically, a pulsometer worn on the wrist comprising a case that contains an electronic optical device for measuring the pulse of the person wearing the pulsometer and an electronic circuit for processing the measurements in order to calculate the pulse, a tightening wristband which holds the back cover of the case pressed against the wrist, wherein the electronic optical measuring device comprises at least one light source and several light receivers, which are arranged in the back cover of the case and which are oriented towards the wrist.

This type of pulsometer is disclosed in particular in U.S. Pat. No. 2003/0065269. In this document, the electronic optical measuring device comprises an emitting diode, which is arranged at the centre of a defined square by four photodiodes, such that each photodiode is located at an equal distance from the emitting diode.

Although this arrangement of the diode and the photodiodes generally gives good results, problems of reliability of the pulse measurements are sometimes observed, particularly because of physiological differences between the various wearers, for example as regards the vascularization of the wrist. These problems of measurement reliability can also appear because of poor positioning of the case on the wrist.

It is an object of the invention to overcome these drawbacks by proposing a simple and economical solution.

Thus, the invention proposes a pulsometer of the type previously described, characterized in that the electronic optical measuring device comprises at least two light sources and at least two light receivers, in that the light sources and the receivers are arranged in the form of a matrix including two lines, each oriented along an orthogonal direction to the direction of the wrist, and at least two columns, oriented parallel to the direction of the wrist, in that each line of the matrix alternately contains one light source and one receiver, and each column of the matrix contains one light source and one receiver.

Owing to the arrangement according to the invention, an increase in the measurement reliability has been observed despite the fact that the receivers are not distributed symmetrically around each light source. In particular, shifting the light source and receiver columns along an orthogonal direction to the direction of the wrist covers a large variety of different physiological characteristics among wearers, which compensates for vascularization differences.

The arrangement according to the invention also allows poor positioning of the pulsometer case on the wrist to be more easily detected, which allows the wearer to detect the cause of pulse measurement errors more easily.

Preferably, the distance between each light source and the adjacent receiver in one line of the matrix is substantially equal to the distance between each light source and the adjacent receiver in one column of the matrix. This arrangement facilitates processing of the signal produced by each receiver by homogenising the intensity of the signals.

According to an advantageous embodiment, the matrix comprises three columns, and the first line contains one light source surrounded by two receivers, and the second line contains a receiver surrounded by two light sources. This arrangement offers a particularly efficient compromise by covering a larger number of different wearer physiologies while producing a compact and economical electronic optical measuring device. In particular, this arrangement minimises the surface occupied on the back cover of the case, particularly in the direction of the wrist, compared to a device according to the prior art.

Within the scope of the present invention, it was unexpectedly observed that the asymmetrical arrangement of the receivers relative to the light sources did not decrease the reliability of the signals produced by the receivers. On the contrary, this arrangement allows at least one reliable reception signal to be obtained in most cases, whatever the morphology of the wearer and his vascularization characteristics.

Preferably, each light source is formed by a diode which emits light within the infrared range, and each receiver is formed by a photodiode. This optical measuring system offers the best results as regards measurement reliability and quality, while being economical and simple to implement.

According to an advantageous embodiment, the electronic circuit includes a pulse calculation unit, which calculates a pulse value respectively corresponding to each reception signal produced by a receiver and to a virtual signal obtained by a virtual signal calculation unit, which corresponds to addition of the reception signals produced by each of the receivers. A selection unit determines an optimum pulse value from among the pulse values obtained by the pulse calculation unit. This solution further increases the diversity of signals that can be exploited and compensates for measurement errors between the different receivers.

Advantageously, the electronic circuit includes a unit for calculating a measurement reliability index, which is a function of the pulse values obtained by the pulse calculation unit. This reliability index makes the best use of the diversity of signals generated by the receivers by avoiding displaying unrealistic pulse values and by informing the user as to the quality of the measurements carried out. Moreover, when the reliability index reaches a determined value, the electronic circuit can detect poor positioning of the case on the wrist or a state wherein the pulsometer is not being worn.

The invention also proposes a control method for a pulsometer according to any of the preceding features, comprising a measuring step during which each light source emits a light beam and each receiver generates a reception signal as a function of the light received, and a pulse calculating step during which a pulse value is calculated from the reception signal generated by each receiver during the measuring step, characterized in that a step of calculating a virtual signal corresponding to an addition of the reception signals generated by each of the receivers is inserted between the measuring step and the calculating step, in that a pulse value is calculated from the virtual signal during the pulse calculating step, and in that, during the selection step, the optimum pulse value is selected from among the pulse values obtained in the pulse calculating step.

According to other features of this method:

the pulse calculating step is followed by a measurement reliability index calculating step during which a comparison is made between the pulse values obtained in the pulse calculating step, the measurement reliability index calculating step is followed by a step of detecting the positioning state of the case during which, as a function of the reliability index value, it is determined whether the pulsometer is being worn or if the case is poorly positioned on the wrist.

Other features and advantages of the present invention will appear more clearly upon reading the following detailed description, made with reference to the annexed drawings given by way of non-limiting example and in which.

Figure 1:
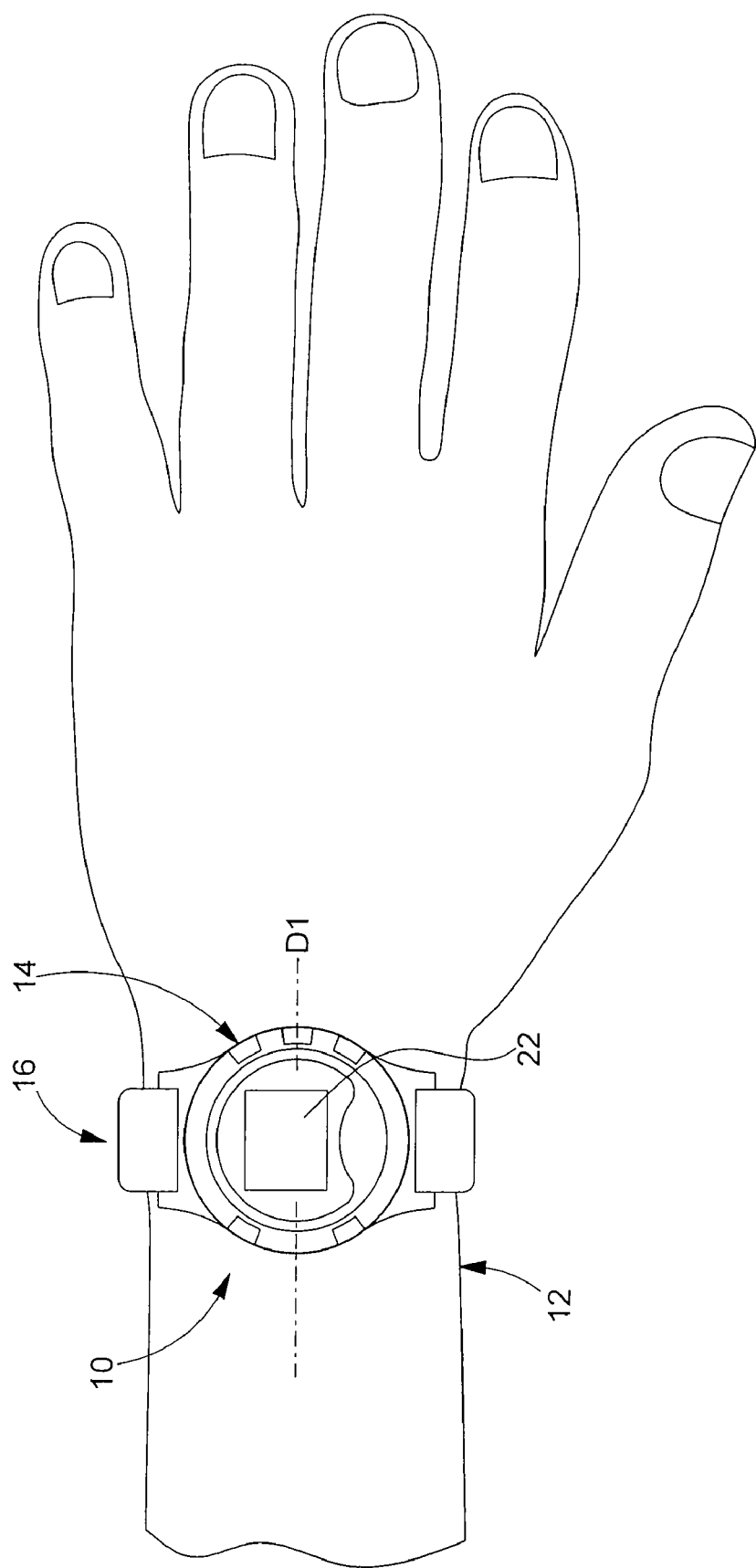
FIG. 1 is a top view that schematically shows the pulsometer according to the invention worn on a wearer's wrist.

FIGS. 1 to 4 show a pulsometer 10 able to be worn on a wearer's wrist 12. Pulsometer 10 comprises a case 14 attached to wrist 12 via a tightening wristband or bracelet 16.

In the following description, the general direction of the forearm associated with wrist 12 of the wearer will be designated by direction D1.

Case 14 contains an electronic optical device 18 for measuring the wearer's pulse and an electronic circuit 20 for processing measurements in order to calculate and display the wearer's pulse P by means of a display device 22 such as a liquid crystal display.

The electronic optical measurement device 18 is arranged in the back cover 24 of case 14, on the opposite side to display device 22. Wristband 16 holds back cover 24 of case 14 pressed against wrist 12, so as to optimise the operation of electronic optical measurement device 18.

In accordance with the teaching of the invention, electronic optical measurement device 18 comprises at least two light sources E1, E2, E3 and at least two light receivers R1, R2, R3, which are oriented towards the wearer's wrist 12 and which are arranged in the form of a matrix including two lines L1, L2 oriented along an orthogonal direction to direction D1 of wrist 12, and at least two columns C1, C2, C3, oriented parallel to the direction D1 of the wrist. Moreover, each line L1, L2 of the matrix alternately contains a light source E1, E2, E3 and a receiver R1, R2, R3, and each column C1, C2, C3 of the matrix alternately contains a light source E1, E2, E3 and a receiver R1, R2, R3.

According to a preferred embodiment, which is shown in the Figures, electronic optical measurement device 18 comprises three light sources E1, E2, E3, formed by three diodes emitting in the infrared range, and three receivers R1, R2, R3, formed by three photodiodes each producing a reception signal SR1, SR2, SR3 which is a function of the quantity of light received.

Figure 2:
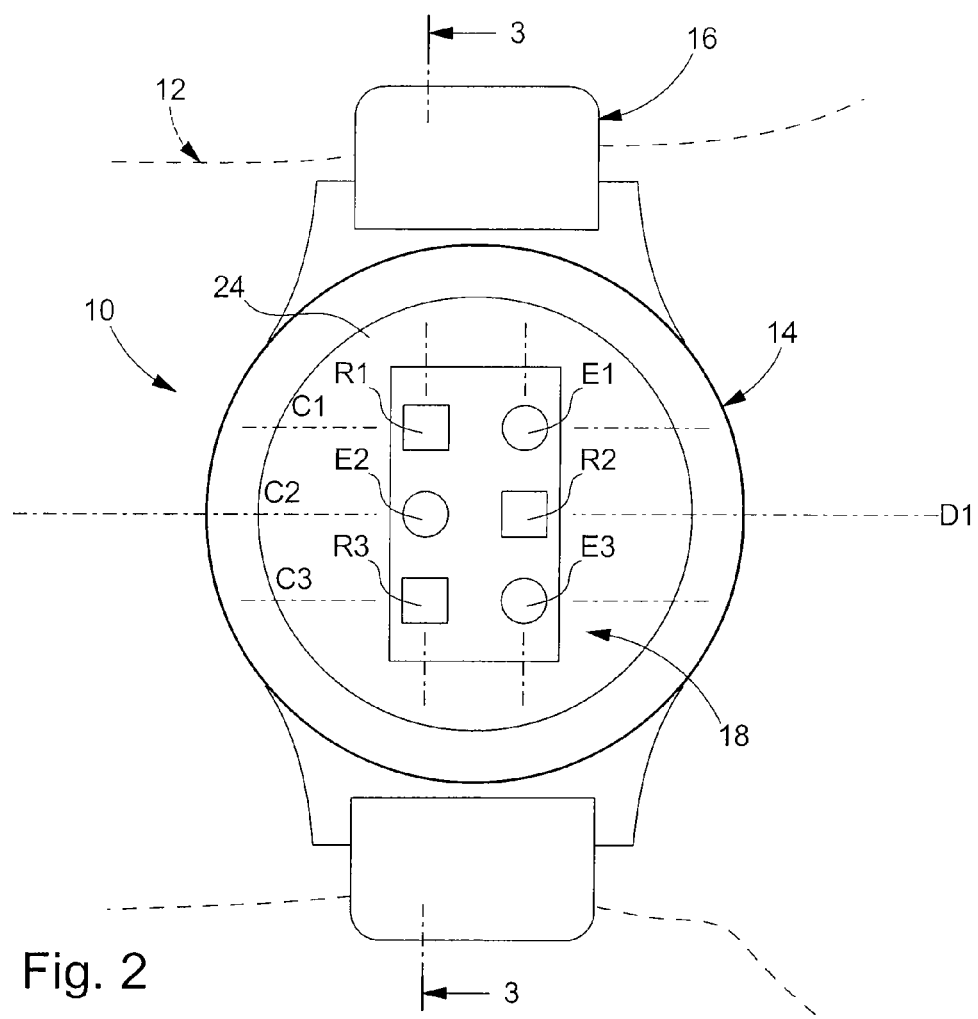
FIG. 2 is a bottom view that schematically shows the back cover of the pulsometer case of FIG. 1 and the electronic optical pulse measurement device thereof.
Figure 3:
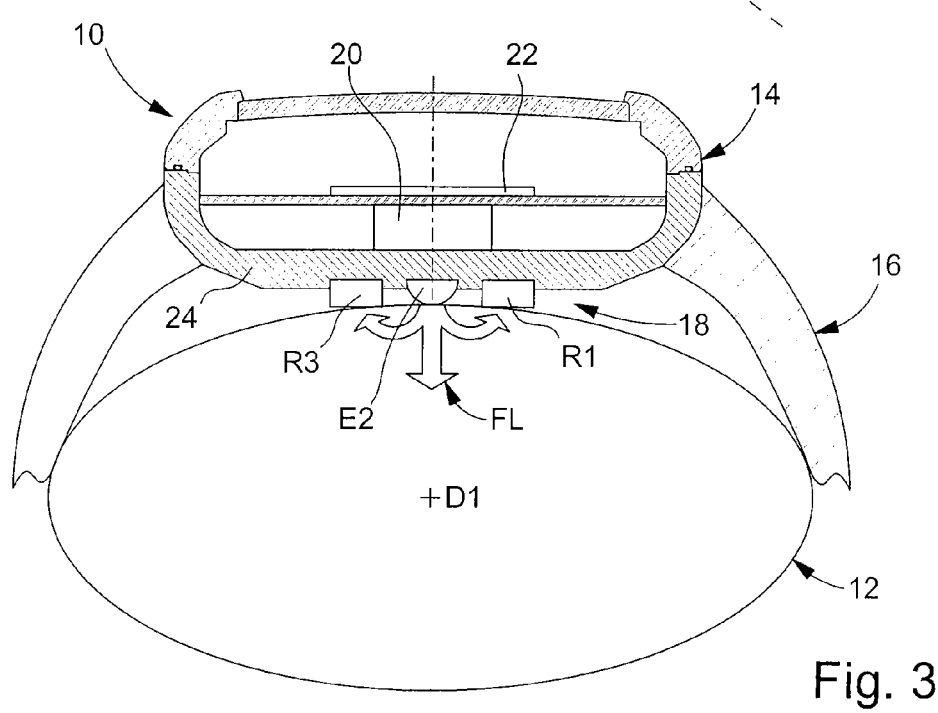
FIG. 3 is a cross-section along the line 3-3 that shows schematically the pulsometer of FIG. 1 and the light beam emitted by a light source of the electronic optical measurement device.

The matrix thus comprises here three columns C1, C2, C3 with, considering FIG. 2, a first column C1 comprising a first receiver R1 in the first line L1 and a first light source E2 in the second line L2, a second column C2 comprising a second light source E2 in the first line L1 and a second receiver R2 in the second line L2, and a third column C3 comprising a third receiver R3 in the first line L1 and a third light source E3 in the second line L2.

In the first line L1, the second light source E2 is thus substantially aligned with the first and third receivers R1, R3. In the second line L2, the first and third light sources E1, E3 are thus substantially aligned with the second receiver R2.

Preferably, the distance between each light source E1, E2, E3 and the adjacent receiver R1, R2, R3 in a line L1, L2 of the matrix is substantially equal to the distance between each light source E1, E2, E3 and the adjacent receiver R1, R2, R3 in a column C1, C2 of the matrix.

According to the embodiment shown in the Figures, lines L1, L2 are rectilinear but they could also be bent and describe two substantially parallel or secant arcs of a circle.

Figure 4:
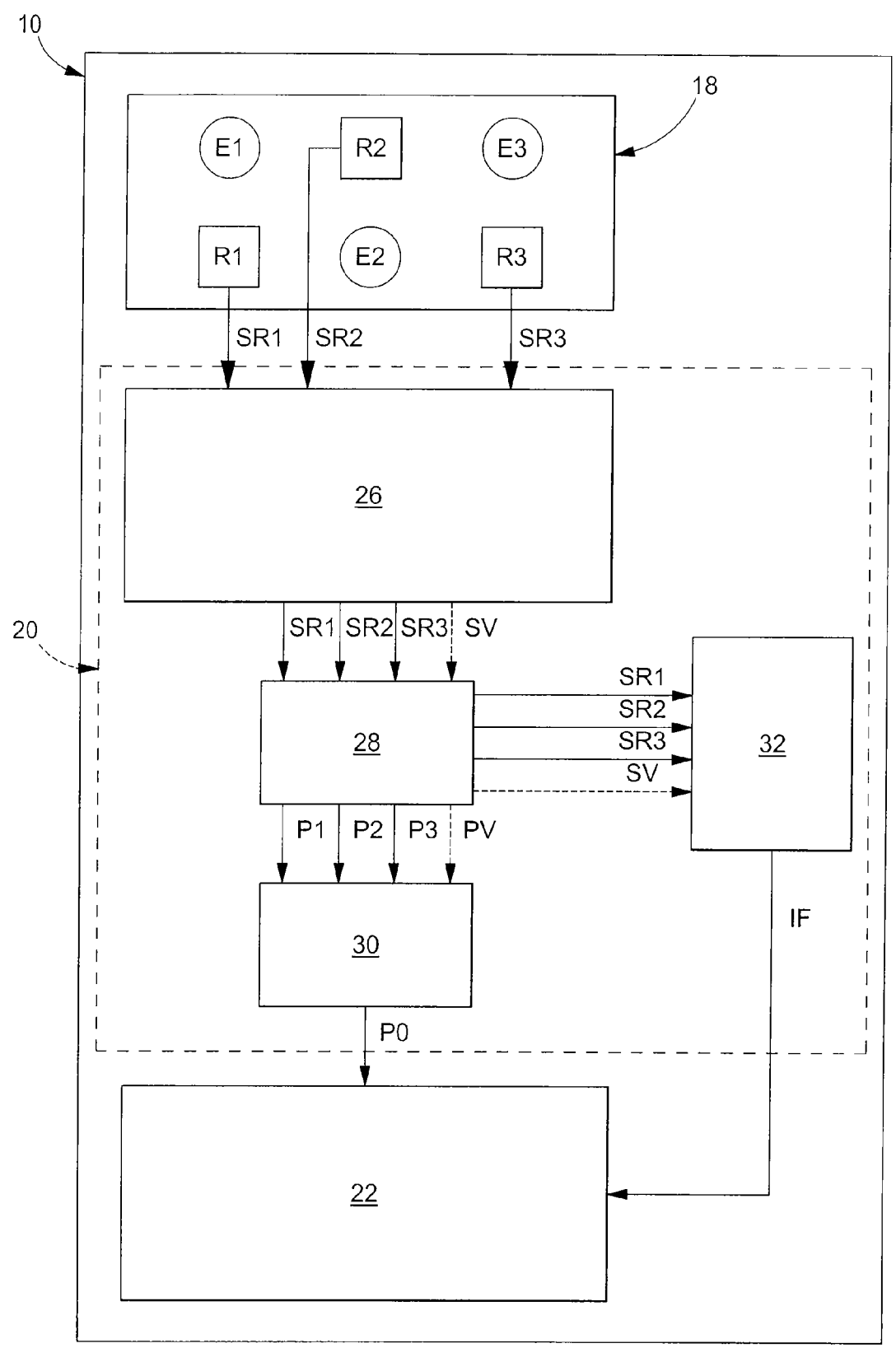
FIG. 4 is a flow chart that shows the pulsometer of FIG. 1 and the electronic circuit fitted thereto.

FIG. 4 shows in more detail the electronic circuit 20 of pulsometer 10 according to the invention.

According to the preferred embodiment, electronic circuit 20 comprises a first calculation unit 26, which determines, from reception signals SR1, SR2, SR3 generated by the three receivers R1, R2, R3 during each pulse measurement, an associated virtual reception signal SV. The virtual reception signal SV is preferably formed by an addition of the three reception signals SR1, SR2, SR3.

Electronic circuit 20 comprises a second calculation unit 28, which determines, from reception signals SR1, SR2, SR3 generated by receivers R1, R2, R3 and from virtual signal SV, the corresponding pulse values P1, P2, P3 and PV. The second calculation unit 28 is provided for processing signals SR1, SR2, SR3, SV and removing noise, for example using filters (not shown), this noise being mainly due to the micro-movements of case 14 relative to the wearer's wrist 12.

Electronic circuit 20 comprises a selection unit 30, which selects, from among pulse values P1, P2, P3, PV obtained by the second calculation unit 28, an optimum pulse value PO. This optimum pulse value PO is selected on the basis of criteria defined by design, for example the pulse value P1, P2, P3, PV possessing the smallest variance is selected as the optimum value PO.

The optimum pulse value PO selected by selection unit 30 is transmitted to display device 22 to allow the wearer to see it.

Of course, from the optimum pulse value PO, other parameters linked to pulse value PO could also be calculated and displayed, for example the quantity of calories consumed, or other data linked to the pulse measurement history.

According to the preferred embodiment, electronic circuit 20 comprises a third calculation unit 32, which determines the value of a pulse measurement reliability index IF from pulse values P1, P2, P3, PV obtained by the second calculation unit 28. The third calculation unit 32 affects a reliability index value IF which is, for example, a function of the signal frequency corresponding to the pulse values P1, P2, P3, PV, of the correlation between these signals, of the amplitude of these signals, and the history of pulse values P1, P2, P3, PV.

As regards the frequency, the signals must be comprised within a determined spectral band.

When several signals are correlated, i.e. when several signals give the same data, particularly having similar variances at the same moment, this indicates that this data is reliable since the spatial diversity of receivers R1, R2, R3 means that they are affected differently when case 14 is poorly positioned.

The amplitude of these signals must be comprises within determined limits, such that too high an amplitude detects a problem of measurement reliability due to the wearer's movements.

Determination of reliability index IF uses for example the result of the variance and dispersion calculations for pulse values P1, P2, P3, PV.

According to a variant of the invention, the third calculation unit 32 can also use reception signals SR1, SR2, SR3 and the virtual signal SV to determine the reliability index value IF.

Third calculation unit 32 can transmit the reliability index value IF to display device 22 to inform the wearer as to the reliability of the pulse values P that are being displayed. As a function of the reliability index value IF, when the latter is representative of insufficient measurement reliability, electronic circuit 20 can also suspend the display of pulse P, so as not to display erroneous pulse values P.

Advantageously, as a function of the reliability index value IF, electronic circuit 20 can detect poor positioning of case 14 on wrist 12, which results in a greater quantity of ambient light reaching a least one of receivers R1, R2, R3.

Within the scope of the present invention, after numerous experiments and trials, it was observed that the configuration according to the preferred embodiment with three light sources E1, E2, E3 and three receivers R1, R2, R3 offers the best compromise for improving the pulse measurement reliability while covering a large number of wearers with different physiological characteristics, yet limiting the space requirement and complexity of electronic optical measuring device 18. Moreover, it is this configuration that gives the best results for detecting problems of poor positioning of case 14 on wrist 12.

It will be noted that, in the preferred embodiment, the second receiver R2, which is located at the centre of second line L2 and which is thus surrounded by three light sources E1, E2, E3, receives light from these three light sources E1, E2, E3 whereas each of the other two receivers R1, R3 essentially receive light from the two adjacent light sources, respectively E1, E2 and E2, E3. In order to compensate for this unbalance in the reception of light, the gain is decreased in the channel of the electronic analogue circuit processing the reception signal SR2 produced by the second receiver R2. Alternatively, the aforementioned unbalance of signal SR2 could be digitally corrected by calculation unit 26.

The method for controlling the pulsometer according to the invention will now be described.

This method comprises a measuring step, implemented by the electronic optical measuring device 18, during which each light source E1, E2, E3 emits a light beam FL directed towards the wearer's wrist 12. This light beam FL propagates in wrist 12 and a part of the light beam FL is back scattered and detected by receivers R1, R2 and R3. As a function of the light received, each receiver produces a reception signal SR1, SR2, SR3 which measures the cardiac pulses of the wearer by detecting periodic variations in the light energy absorbed by the wearer's tissues.

The principle of this pulse P measuring step is disclosed in particular in U.S. Pat. No. 2003/0065269 to which reference can be made for more detail, in particular in the preamble of the description of this document.

In accordance with the teaching of the invention, the pulse P measuring step is followed by a virtual signal SV calculating step, implemented by the first calculation unit 26, during which virtual signal SV corresponding to an addition of reception signals SR1, SR2, SR2, is produced.

The virtual signal SV calculating step is followed by a step of calculating pulse P1, P2, P3, PV, implemented by the second calculation unit 28, during which reception signals SR1, SR2, SR3 and virtual signal SV are processed to determine the corresponding pulse values P1, P2, P3, PV.

The pulse calculating step is followed by a selection step, implemented by selection unit 30, during which the optimum pulse value PO is selected from among the pulse values P1, P2, P3, PV obtained during the pulse calculating step. It is this optimum pulse value PO that is displayed.

Preferably, the pulse calculating step is followed by a step of calculating the measurement reliability index IF, implemented by the third calculation unit 32, during which the pulse values P1, P2, P3 corresponding to reception signals SR1, SR2, SR3 and the pulse value PV corresponding to virtual signal SV are compared to each other so as to determine the value of reliability index IF representative of the reliance that can be placed on the measurements carried out and on the optimum pulse value PO obtained by selection unit 30.

It will be noted that the step of calculating reliability index IF can compare the pulse values P1, P2, P3, PV obtained from the pulse calculating step in progress to the preceding values which were obtained during the calculating steps corresponding to the preceding measurements and which have been stored, which determines whether the development of the pulse value PO over time is realistic.

Reliability index IF can be calculated by taking account of the amplitude values of the continuous and alternating components of each pulse value P1, P2, P3, PV due to the ambient light, and the amplitude values of the continuous and alternating components of each signal P1, P2, P3, PV due to the light emitted by sources E1, E2, E3, and taking account of values derived from these signals P1, P2, P3, PV, such as for example variance or the frequency spectrum. By taking account of these parameters, it is thus possible to distinguish the case where pulsometer 10 is poorly positioned on wrist 12 from the case where pulsometer 10 is not being worn, for example when it is placed on a table.

Advantageously, the reliability index IF calculating step is followed by a step of detecting when case 14 is poorly positioned on wrist 12 or a state in which pulsometer 10 is not being worn during which, as a function of the value of reliability index IF, electronic circuit 20 indicates the poor position to the wearer, for example by means of display device 22, or electronic circuit 20 interrupts the pulse display if a non-worn state is detected.

What is claimed is:

1. A pulsometer worn on the wrist including a case, which contains an electronic optical device for measuring the pulse of the wearer of the pulsometer and an electronic circuit for processing the measurements in order to calculate the pulse, a tightening wristband, which holds a back cover of the case pressed against the wrist, wherein the electronic optical measuring device includes at least one light source and several light receivers which are arranged in the back cover of the case and which are oriented towards the wrist, wherein the electronic optical measuring device includes at least two light sources and at least two receivers, wherein the light sources and the receivers are arranged in the form of a matrix including two lines each oriented along an orthogonal direction to the direction of the wrist, and at least two columns oriented parallel to the direction of the wrist, wherein each line of the matrix alternately contains a light source and a receiver, and each column of the matrix alternately contains a light source and a receiver.

2. The pulsometer according to claim 1, wherein the distance between each light source and the adjacent receiver in one line of the matrix is substantially equal to the distance between each light source and the adjacent receiver in one column of the matrix.

3. The pulsometer according to claim 1, wherein the matrix includes three columns and wherein the first line contains one light source surrounded by two receivers, and the second line contains one receiver surrounded by two light sources.

4. The pulsometer according to claim 2, wherein the matrix includes three columns and wherein the first line contains one light source surrounded by two receivers, and the second line contains one receiver surrounded by two light sources.

5. The pulsometer according to claim 1, wherein each light source is formed by a diode which emits light in the infrared range, and each receiver is formed by a photodiode.

6. The pulsometer according to claim 1, wherein the electronic circuit includes a pulse calculating unit which calculates a pulse value corresponding respectively to each reception signal produced by a receiver and a selection unit which determines an optimum pulse value from among the pulse values obtained by the pulse calculating unit.

7. The pulsometer according to claim 1, wherein the electronic circuit includes a unit for calculating a virtual signal corresponding to an addition of the reception signals produced by each of the receivers, a pulse calculating unit which calculates a pulse value corresponding respectively to each reception signal produced by one receiver and to the virtual signal, and a selection unit which determines an optimum pulse value from among the pulse values obtained by the pulse calculating unit.

8. The pulsometer according to claim 6, wherein the electronic circuit includes a unit for calculating a measurement reliability index which is a function of the pulse values obtained by the pulse calculating unit.

9. The pulsometer according to claim 7, wherein the electronic circuit includes a unit for calculating a measurement reliability index which is a function of the pulse values obtained by the pulse calculating unit.

10. The control method for a pulsometer according to claim 1, including a measurement step during which each light source emits a light beam and each receiver produces a reception signal as a function of the light received, and a pulse calculating step during which a pulse value is calculated from the reception signal produced by each receiver during the measuring step, wherein the pulse calculating step is followed by a selection step during which an optimum pulse value is selected from among the pulse values obtained in the pulse calculating step.

11. The control method for a pulsometer according claim 1, including a measuring step during which each light source emits a light beam and each receiver produces a reception signal as a function of the light received, and a pulse calculating step during which a pulse value is calculated from the reception signal produced by each receiver during the measuring step, wherein a step of calculating a virtual signal corresponding to an addition of the reception signals produced by each of the receivers is inserted between the measuring step and the pulse calculating step, wherein a pulse value is calculated from the virtual signal, during the pulse calculating step, and wherein, during the selection step, the optimum pulse value is selected from the pulse values obtained in the pulse calculating step.

12. The control method according to claim 10, wherein the pulse calculating step is followed by a step of calculating a measurement reliability index during which a comparison is made between the pulse values obtained in the pulse calculating step.

13. The control method according to claim 11, wherein the pulse calculating step is followed by a step of calculating a measurement reliability index during which a comparison is made between the pulse values obtained in the pulse calculating step.

14. The control method according to claim 12, wherein the measurement reliability index calculating step is followed by a step of detecting the positioning step state of the case during which, as a function of the reliability index value, it is determined whether the pulsometer is being worn or whether the case is poorly positioned on the wrist.

15. The control method according to claim 13, wherein the measurement reliability index calculating step is followed by a step of detecting the positioning step state of the case during which, as a function of the reliability index value, it is determined whether the pulsometer is being worn or whether the case is poorly positioned on the wrist.

* * * * *